United States Patent [19]

Cregg et al.

[11] Patent Number: 5,122,465

[45] Date of Patent: Jun. 16, 1992

[54] **STRAINS OF *PICHIA PASTORIS* CREATED BY INTERLOCUS RECOMBINATION**

[75] Inventors: James M. Cregg, San Diego; Mary E. Digan, Mountain View, both of Calif.

[73] Assignee: Phillips Petroleum Company, Bartlesville, Okla.

[21] Appl. No.: 365,072

[22] Filed: Jun. 12, 1989

[51] Int. Cl.$^5$ .............. C12N 15/00; C12N 1/14; C12N 1/16

[52] U.S. Cl. ............... 435/172.3; 435/254; 435/255; 435/256; 935/28; 935/97

[58] Field of Search .............. 435/172.3, 254, 255, 435/256, 320; 935/28, 97

[56] References Cited

U.S. PATENT DOCUMENTS 4,812,405  3/1989  Lair et al. .................... 435/172.3

OTHER PUBLICATIONS

Sherman, *Methods in Yeast Genetics*, Cold Spring Harbor, pp. 9–129, 1982.
H. Klein & T. Petes: Intrachromosomal Gene Conversion in Yeast; Nature; 289, 144–148 (1981).
J. Jackson & G. Fink: Meiotic Recombination Between Duplicated Genetic Elements in Saccharomyces Cerevisiae; Genetics 109, pp. 303–332 (1985).
S. Jinks-Robinson & T. Petes, High-Frequency Meiotic Gene Conversion Between Repeated Genes on Nonhomologous Chromosomes in Yeast; Proc. Natl. Acad. Sci., USA, 82, pp. 3350–3354 (1985).
Hybridization and Genetic Analysis of the Methanol Yeasts Pichia pinus; Genetika, 13, No. 2, pp. 322–329, (1976).
J. Jackson & G. Fink, Gene Conversion Between Duplicated Genetic Elements in Yeast; Nature 292, 306–311 (1981).
H. Rudolph et al., One-Step Gene Replacement in Yeast by Cotransformation; Gene 36, 87–85, (1985).
A Method for Gene Disruption . . . Alani et al., Genetics 116:541–545 (1987).
Functional Characterization of Two Alcohol Oxidase Genes, Cregg et al., Molecular & Cellular Bio., vol. 9, No. 3, pp. 1316–1323 (1989).

*Primary Examiner*—Robin L. Teskin
*Attorney, Agent, or Firm*—J. E. Phillips

[57] ABSTRACT

A process for the regeneration of a selectable phenotype at a high frequency by interlocus recombination, in yeast cultures transformed with recombinant DNA constructs comprised of a gene whose product complements the selectable phenotype to be regenerated is disclosed. A sequence of steps is involved including: suspending together in rich media mutant yeast strains, plating onto presporulation agar, replica plating onto other agar media suitable for selection and growth of diploid cells, plating on sporulation agar or alternatively dissecting the asci, digesting the cells, growing the spores on minimal media, and screening for the desired phenotype.

7 Claims, 1 Drawing Sheet

MATING OF PICHIA STRAINS PPF1 AND kM7121

STRAINS OF *PICHIA PASTORIS* CREATED BY INTERLOCUS RECOMBINATION

The invention relates to the field of recombinant DNA technology. In one aspect, the invention relates to a process for regeneration of selectable marker genes in strains of *Pichia pastoris*.

BACKGROUND

The key to transformation of most organisms is the selectable marker gene, which allows one to identify and selectively grow transformed cells in the presence of a vast majority of untransformed cells. Unlike transformation of extensively studied organisms, such as *Escherichia coli* and *Saccharomyces cerevisiae*, transformation of many prokaryotic, and lower eukaryotic organisms is dependent on a limited number of selectable markers. Since transformation with a vector containing a marker gene normally results in the permanent loss of the selectable phenotype associated with that marker, it is difficult to proceed with further recombinant DNA-based modifications.

In organisms that are not genetically well-developed, the limited number of available marker genes can be a significant experimental handicap. Since the development of new markers requires considerable time and effort, it would be advantageous if methods existed to preserve or regenerate markers.

In some instances, a marker can be preserved by integrating markerless DNA fragments into the genome through cotransformation with an autonomously replicating, marker-bearing plasmid which is subsequently cured from the strain (Rudolf et al., 1985; Cregg et al., 1989). However, such a marker cannot be used for selective growth.

A method to regenerate markers has been described by Alani et al. (1987). This method employs an orotidine-5' phosphate decarboxylase gene (URA3) as marker and a powerful positive selection scheme that utilizes the drug, 5-fluro-orotic acid (Boeke et al., 1984), to select strains which have become Ura-, as a result of mitotic recombination events between repeated sequences placed on each side of URA3. However, this selection scheme requires a URA3-defective host organism which is not currently available in *Pichia pastoris*. To utilize markers presently available for Pichia, excision event products must be found by screening for loss of marker phenotype, a process which is likely to be tedious and may be fruitless, depending on the rate at which such events occur in Pichia. Consequently, a more exacting method, capable of high frequency regeneration of selectable gene markers, would be a major improvement over the present state of the art.

OBJECT OF THE INVENTION

Thus, an object of the present invention is to provide a process for the regeneration of a selectable phenotype at high frequency in strains of *Pichia pastoris* which have been transformed with recombinant DNA constructs comprised of a gene whose product complements the selectable phenotype to be regenerated.

These and other objects of the invention will become apparent from inspection of the disclosure and claims herein provided.

STATEMENT OF INVENTION

In accordance with the present invention, there has been developed a process for the regeneration, by interlocus recombination, of a selectable phenotype in mutant yeast strains of the species *Pichia pastoris*, said strains having been transformed with recombinant DNA constructs comprised of a gene whose product complements the selectable phenotype to be regenerated. Such "regenerated" strains are useful hosts for transformation with recombinant DNA constructs comprised of a gene whose product complements the selectable phenotype that was regenerated.

DETAILED DESCRIPTION OF THE INVENTION

Figure 1:
Figure 1:
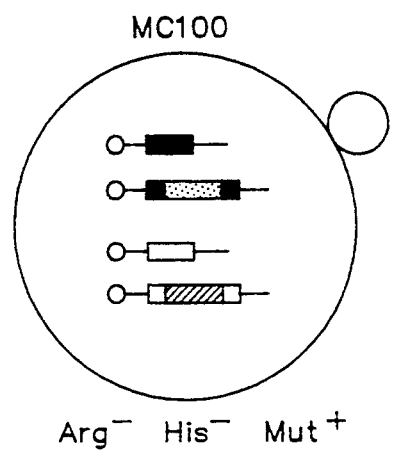
Figure 1:
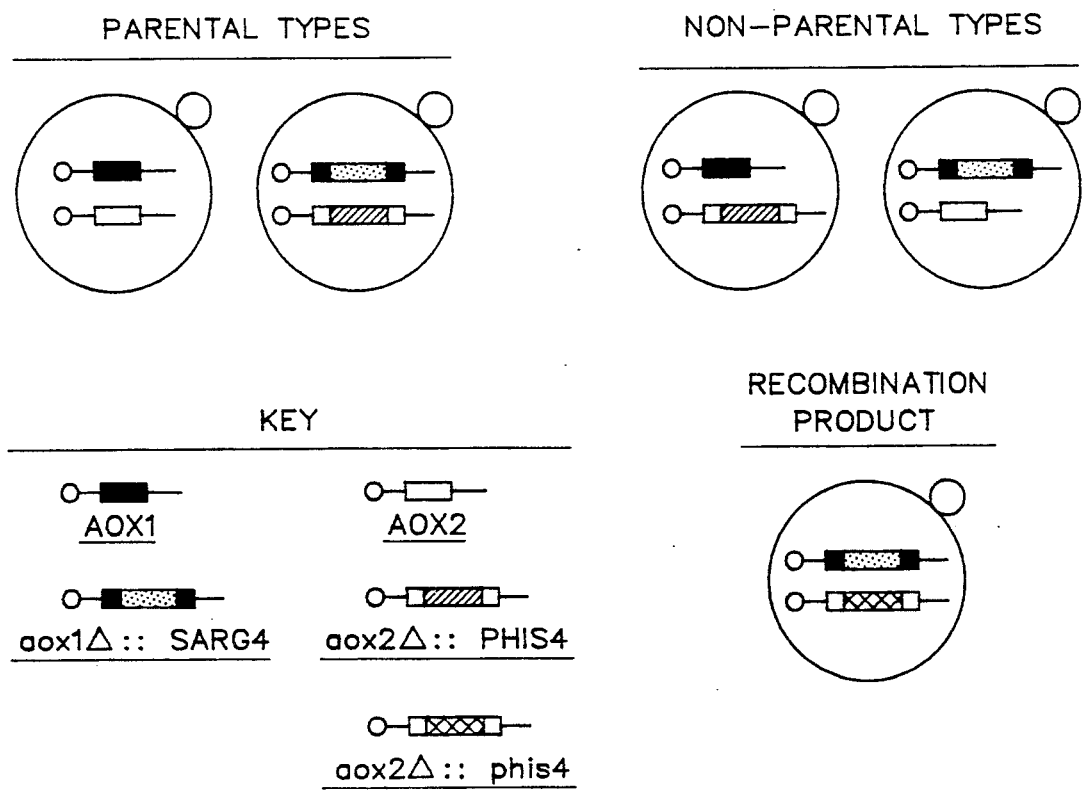

The following definitions are provided for clarity.

DEFINITIONS

Phenotypic/phenotype—The visible properties of an organism that are produced by the interaction of genotype and the environment. The phenotype of a cell refers to its appearance or behavior under specified conditions. The phenotype of a HIS4 cell differs from a his4 cell in that the former can utilize histidine whereas the latter cannot.

Allele—When a gene exists in more than one form each form is called an allele. The wild type form of the HIS4 gene is one allele, and the mutant form, his4, is another allele.

Haploid—A cell is considered haploid if it contains only one copy of each chromosome; diploid cells have two copies of each chromosome.

Loci/locus—The position in a chromosome of a particular gene or allele. Each gene occupies a specific position on a chromosome; that position is its locus.

Meiosis—A type of cell division that reduces the number of chromosomes by half and that involves a reductional division in which one of each pair of homologous chromosomes passes to each daughter cell. A diploid cell undergoes meiosis to form haploid cells.

Interlocus alleles—Two alleles of the same gene will usually reside at the same locus in different cells. The term interlocus allele refers to the situation where the location of an allele is other than its usual chromosomal position. For instance, when the HIS4 gene is inserted into the AOX1 gene by recombinant techniques, the transferred HIS4 gene now resides at an interlocus in relation to the endogenous HIS4 gene and can be referred to as an interlocus allele.

Genotype/genotypic—All or part of the genetic constitution of an organism. The genotype of a cell refers to the specific alleles it has.

Recombination—The joining of genes, sets of genes, or parts of genes, into new combinations, either biologically or through laboratory manipulation.

We have discovered that meiosis, which occurs during the mating and sporulation process, stimulates recombination events between two interlocus alleles, resulting in the frequent exchange of information from one allele to the other. We have further discovered that interlocus recombination during meiosis can be used to regenerate the selectable phenotype in previously transformed strains if one of the parent Pichia pastoris strains contain two phenotypically distinguishable alleles of a gene present at different positions (loci), whether the loci be on different chromosomes or on the same chromosome within its haploid genome of *Pichia pastoris*.

After matings involving a parent strain such as that described above, offspring or spore products are frequently isolated in which information that determines the phenotypic and genotypic identity of one allele has moved to the other allele.

For instance, after integrative transformation of a mutant host, that is auxotrophic due to the presence of a mutant allele of a gene, with vector DNA that comprises as its selectable marker the wild-type allele of the same gene, the transformed host is prototrophic with respect to that phenotype. This prototrophic host cannot be a host for a second transformation with any vector that contains the same wild-type gene as the selectable marker because there is no means for selecting positive transformants. However, an interlocus recombination event can result in the replacement of the wild-type allele with a mutant allele, while maintaining the mutant allele information at the mutant locus as well. Thus, strains arising after this type of interlocus recombination event contain only mutant alleles and are once again auxotrophic. Such strains can now be transformed a second time with vectors relying on the same selectable marker gene. After a second transformation, this marker regeneration process can be repeated to prepare a host capable of a third transformation with vectors having the same marker and so on. Thus, a strain could potentially be transformed an unlimited number of times using vectors that had the same selectable marker gene. This process might be useful for the insertion of multiple copies of heterologous gene expression cassettes into the genome of *Pichia pastoris.*

As described in one of the examples, a His+ parent strain having a wild-type allele of the HIS4 gene present at the AOX2 locus, due to integration of a recombinant expression cassette which employed the wild-type HIS4 gene for selection at the AOX2 locus, recombined with the mutant his4 allele present at the normal HIS4 gene locus. This interlocus recombination resulted in the generation of a recombinant which now contained mutant his4 allele information at the AOX2 locus as well as the native HIS4 locus. Because the new recombinant now has only mutant HIS4 alleles, it is phenotypically His- and can be transformed again with recombinant DNA which employs the wild-type HIS4 gene for selection.

In accordance with the present invention, mutant strains of yeast of the species *Pichia pastoris* transformed with recombinant DNA constructs comprised of a gene whose product complements the selectable phenotype, are capable of repetitive regeneration of the selectable phenotype at high frequency, via recombination, during a mating process which comprises:

(a) suspending together in a rich media a first and second mutant strain of the species *Pichia pastoris*, said first mutant being a *Pichia pastoris* strain which contains two phenotypically distinguishable alleles of a gene present at different positions (loci) within the haploid genome of *Pichia pastoris*, and said second mutant being a *Pichia pastoris* strain which contains a second auxotrophic mutation so that diploid strains resulting from mating of the first and second strains may be selected.

(b) plating the suspension containing said first and second mutant yeast strains prepared in accordance with step (a) on presporulation agar and maintaining plates at about 30° C. for about 12-48 hours, preferably about 24 hours;

(c) replica plating the cells produced in accordance with step (b) onto sporulation agar and maintaining the resulting plates at about 30° C. for about 8-48 hours, preferably about 24 hours;

(d) replica plating the cells produced in accordance with step (c) onto agar medium suitable for selection of diploid cells and maintaining at about 25°-35° C. for 1-5 days, or until colonies are visible;

(e) suspending individual diploid colonies obtained from step (d) in rich media;

(f) plating the suspension produced in accordance with step (e) on presporulation agar and maintaining the resulting plates at about 30° C. for about 12-48 hours;

(g) replica plating the cells produced in accordance with step (f) onto sporulation agar and maintaining the resulting plates at about 30° C. for 3-5 days;

(h) alternatively (1) dissecting the 4-spored asci produced in accordance with step (g), or (2) removing the cells from the sporulation plates, resuspending the cells in phosphate buffered media and exhaustively digesting the suspended cells with a cell wall degrading reagent;

(i) germinating and growing each spore on minimal medium supplemented with nutrients required for growth of haploid spore products and maintaining at about 30° C. for about 3 hours; and thereafter (j) replica plating the cells in accordance with step (i) onto sets of minimal medium agar plates, supplemented with combinations of nutrients required to distinguish spore product phenotypes, and maintaining at about 30° C. for 1 day; and (k) screening the colonies produced in accordance with step (i) for the appropriate recombinant products.

Suitable mutants for use in the process of the invention are known to those skilled in the art. Exemplary examples include, but are not limited to, *Pichia pastoris* strain KM7121 (arg4 his4 aox1Δ::SARG4 aox2Δ:-PHIS4; deposited as NRRL Y-18019) as a first parent strain, and *Pichia pastoris* PPF1 (arg4 his4; deposited as NRRL Y-18017) as a second parent strain.

The cells to be mated are first suspended in a rich media, such as for example YPD media, and other similar media as well known to those of skill in the art. The suspended cells are plated on presporulation agar, such as GNAP, and maintained at about 30° C. for 12 up to 48 hours.

Once grown on presporulation agar, cells are replica plated to sporulation agar, then maintained at about 30° C. for about 8-24 hours.

Cells grown on the sporulation agar are then replica plated on minimal medium with 0.5% methanol as carbon source, a medium that selects for growth of diploid cells and against growth of either parental type cell, and germinated at about 25°-35° C. for about 1-5 days.

The resultant colonies are suspended in rich media, such as, for example, YPD, plated on presporulation agar as described hereinabove and maintained at about 30° C. for about 12-48 hours, then replica plated onto sporulation agar and maintained at about 30° C. for about 3-5 days. The resulting 4-spored asci are either dissected, or cells are removed from sporulation plates, resuspended in phosphate buffered media and exhaustively digested with a cell wall degrading reagent. As a result of the latter treatment, vegetative cells are destroyed, and only random spores remain to be germinated and grown. While the latter method is preferred for rapid sample generation, the former method (i.e., dissection of the 4-spored asci) is preferred when a statistical population of segregants is desired. The resulting haploid spore-derived colonies grown on rich medium agar, for example YEPD agar, are screened for relevant phenotypes by replica plating on minimal medium agar supplemented with combinations of nutrients required to distinguish phenotypes.

For the KM7121×PPF1 cross described in the Examples, the screening procedure involved germinating and growing the spores on YPD media at about 30° C. for about 2 days, then replica plating the resulting colonies onto minimal medium supplemented with various combinations of glucose, histidine, arginine, and with medium supplemented with methanol, histidine, and arginine.

After incubation for 1 day at 30° C. the colonies on glucose agar were examined for Arg and His phenotypes.

Colonies on methanol agar were examined for growth after 1 week at room temperature.

Prior to this discovery it was not possible to transform Pichia strains auxotrophic at one locus more than once with a DNA fragment comprised of a marker gene to complement the auxotrophy, or Pichia strains auxotrophic at two loci more than twice, one time each with a DNA fragment comprised of a marker gene to complement the first and second auxotrophy, respectively. Further transformations were not possible without an additional marker to select transformed cells. However, in the present invention when a strain, which contains two phenotypically distinguishable alleles of a gene within the haploid genome of *Pichia pastoris* undergoes meiosis, the wild-type gene present at the ectopic location will recombine with the mutant allele at the native location at high frequency. A common result of such a recombination event is a strain with a mutant allele at both the native and ectopic loci. The resulting strain is again auxotrophic and can be further transformed by other DNA fragments containing a gene to complement the auxotrophy as the selectable marker.

The novelty of the invention lies in the fact that, since it is possible to perform this regeneration process after each transformation, it should be possible to transform a Pichia strain an unlimited number of times using the same selectable marker system. An application of the method is the insertion of additional heterologous gene expression cassettes into a genome. Another application is the construction of strains having multiple mutations created by repeated transformation for in depth investigations into the genetic structures and mechanisms in an organism.

The invention will now be described in greater detail by reference to the following non-limiting example.

EXAMPLE

Cross Mating of *Pichia pastoris* Double Auxotrophs

Interlocus recombination was used to regenerate histidine auxotrophy as a selectable phenotype in a strain that was originally prototrophic for arginine and histidine and which could not utilize methanol due to disruption of both the AOX1 and AOX2 genes. The methanol utilization defective phenotype is referred to as Mut−. The strain bearing two alleles of His4 at different loci was KM7121 (arg4 his4 aox1Δ:SARG4 aox2Δ::PHIS4; NRRL Y-18019). This strain was crossed with strain PPF1 (arg4 his4 AOX1 AOX2; NRRL Y-18017). The goal of this cross was to stimulate an interlocus recombination event between the endogenous mutant HIS4 loci and the AOX2-derived wild-type locus to produce a strain like KM7121, but with mutant HIS4 information at AOX2. Since this strain would be defective in both HIS4 genes and therefore His−, it could be further transformed with vectors that contained a HIS4 gene as a selectable marker.

Both strains were defective in their endogenous ARG4 and HIS4 genes. PPF1 was otherwise wild-type. KM7121 contained a defective AOX1 gene due to a previous transformation event which resulted in the disruption of the AOX1 gene by the insertion of the *Saccharomyces cerevisiae* ARG4 gene. KM7121 also contained a defective AOX2 gene due to a second transformation event which resulted in the partial deletion of the AOX2 gene and the insertion of a wild-type HIS4 gene. Because the insertions at the AOX loci resulted in differences in molecular structure at the loci, it was possible to distinguish all four AOX loci (AOX1, aox1Δ::SARG4, AOX2 and aox2Δ::PHIS4) physically by their sizes in Southern blot hybridization experiments. The sizes when digested with EcoRI and probed with an AOX probe were: in PPF1, AOX1, 5.5 kb and AOX2, 7.0 kb; in KM7121, aox1Δ::SARG4, 7.8 kb; and aox2Δ::PHIS4, 8.9 kb.

The mutant strains were crossed as follows:

Approximately $5 \times 10^7$ cells of each strain were mixed and spread onto a GNAP agar plate. The GNAP plate was incubated at 30° C. for about 24 hours and then replica plated onto sporulation medium agar.

This plate was incubated at 30° C. for about 20 hours and replica plated onto a diploid selection plate. Since KM7121 was Arg+ and His+ but could not utilize methanol (Mut−), and PPF1 was Arg− and His− but could utilize methanol (Mut+), diploid cells were selected on agar medium by their ability to grow on an agar selection media composed of minimal medium agar with methanol (0.5%) as a sole carbon and energy source.

After 5 days on the selection agar plates, about 200 colonies appeared. The diploid nature of the Arg+ His+ Mut+ strains was confirmed by Southern blot examination of their AOX loci. DNAs were isolated, digested with EcoRI and probed with a DNA fragment specific for the AOX1 and AOX2 DNA. The diploids contained both AOX1 alleles of 5.5 and 7.8 kb and both AOX2 alleles of 7.0 and 8.9 kb, as expected.

One of these diploid strains (MC100) was sporulated to stimulate recombination and obtain haploid spore products from the cross. Approximately $1 \times 10^6$ cells of the diploid strain were spread on a GNAP plate and treated as described above for the mating procedure, except that the sporulation plate was incubated for 4 days at 30° C. to allow the diploids to complete sporulation. Spores were collected by washing the plates and then subjected to an extensive treatment with Glusulase and Zymolyase, after which they were stored overnight at 4° C. in 0.1M phosphate buffer, pH 7.0. Only spores should survive this treatment, since vegetative cells are far more sensitive to the cell-wall-degrading agents used. A sample of the spore preparation was then diluted and spread on non-selective medium agar (YEPD medium agar). These were incubated for 2 days at 30° C. Each agar plate was then replica-plated onto a series of minimal medium agar plates supplemented with the following: 1) 1% glucose; 2) 1% glucose and 50 μg/ml histidine; 3) 1% glucose and 50 μg/ml arginine; 4) 1% glucose, 50 μg/ml of both arginine and histidine; and 5) 0.5% methanol, 50 μg/ml of both arginine and histidine. After incubation for 1 day at 30° C., colonies on glucose agar were examined for Arg and His phenotypes. Colonies on methanol agar were examined for growth after 1 week at room temperature.

The genotypes of the four spore products expected prior to this discovery from independent segregation of alleles from this PPF1×KM7121 cross are shown diagrammatically in FIG. 1. In addition, one other spore product that was a result of interlocus recombination is shown in FIG. 1. Two expected spore types are identical to the parent strains, PPF1 and KM7121, and are called parental types. Two other spore types are a mixture of the parent strains and are called non-parental types.

One of the expected non-parental spore product types was Arg−His+Mut+ and the Southern blot pattern of the AOX loci from spore-derived strains of this type showed a wild-type AOX1 locus and a PHIS4-disrupted AOX2 locus as predicted from their phenotypes. The other expected and observed phenotype for non-parental spore products type was Arg+His−Mut+/−. The Southern blot patterns of the AOX loci from all of these Arg+His−Mut+/− non-parental spore products showed an SARG4-disrupted AOX1 locus and a wild-type AOX2 locus. The phenotype predicted for spore products that were the result of the desired interlocus recombination event was Arg+His−Mut−. Of 180 spore-derived colonies examined, ten had this phenotype, a high frequency for products of a interlocus recombination event. Southern blot analysis of the AOX loci of two of these recombination-product strains revealed that these strains contained disruptions at both AOX1 and AOX2, identical to that of KM7121, one of the parent strains. In particular, the disruption of AOX2 by a DNA fragment from HIS4 was present. Since these strains were His−, they must have resulted from an interlocus recombination event between one of the endogenous mutant HIS4 alleles and the wild-type allele of AOX2. The recombination event resulted in the transfer of mutant HIS4 information from the endogenous locus to HIS4 at the AOX2 locus. One of these interlocus recombination spore-products was designated MC100-3.

Examples of the media used are given below.

| | |
|---|---|
| YEPD Agar | 2% dextrose |
| | 2% peptone |
| | 1% yeast extract |
| | 2% agar |
| Presporulation Agar (GNAP) | 5% dextrose |
| | 2% peptone |
| | 1% yeast extract |
| | 0.5% agar |
| | 2.3% nutrient agar |
| Sporulation Agar | 0.5 sodium acetate (anhydrous) |
| | 1% KCl |
| | 2% dextrose |
| | 2% agar |
| Minimal Agar | 2% dextrose |
| | 0.675% yeast nitrogen base |
| | (minus amino acids) |
| | 2% agar |
| YPD Medium | 1% Bacto-yeast extract |
| | 2% Bacto-peptone |
| | 2% Dextrose |
| Diploid Selection Agar | 0.675% yeast nitrogen base |
| | (minus amino acids) |
| | 0.5% methanol |
| | 2% agar |

The example has been provided merely to illustrate the practice of the invention and should not be read so as to limit the scope of the invention or the appended claims in any way.

Reasonable variations and modifications, not departing from the essence and spirit of the invention, are contemplated to be within the scope of patent protection desired and sought.

That which is claimed is:

1. A process for regenerating a selectable phenotype in strains of *Pichia pastoris*, said strains having been transformed with a recombinant DNA construct comprising a wild-type allele of a gene whose product confers the selectable phenotype to be regenerated, which process comprises:

(a) suspending together in a rich media a first and second mutant strain, said first mutant strain being a transformed strain of *Pichia pastoris* containing two phenotypically distinguishable alleles of the marker gene present at different positions within the haploid genome of *Pichia pastoris*, and said second strain being a mutant strain of *Pichia pastoris* containing an auxotrophic mutation of the same gene of which the first strain comprises two distinguishable alleles to allow selection of diploids resulting from the mating of said first and second strains;

(b) plating the suspension containing said first and second mutant yeast strains prepared in accordance with step (a) on presporulation agar and maintaining the resulting plates at 30° C. for 12-48 hours;

(c) replica plating the cells produced in accordance with step (b) onto sporulation agar and maintaining the resulting plates at about 30° C. for about 8-48 hours;

(d) replica plating the cells produced in accordance with step (c) on minimal agar medium suitable for selection and growth of diploid cells, and maintaining at 25°-35° C. for 1-5 days.

(e) suspending individual diploid colonies obtained from step (d) in rich media;

(f) plating the suspension produced in accordance with step (e) on presorulation agar and maintaining the resulting plates at about 30° C. for 12-48 hours;

(g) replica plating the cells produced in accordance with step (f) onto sporulation agar and maintaining the resulting plates at about 30° C. for 3-5 days;

(h) alternatively;
      (1) dissecting the 4-spored asci produced in accordance with step (g); or
      (2) removing the cells from the sporulation plates, resuspending the cells in phosphate buffered media and exhaustively digesting the suspended cells with a cell wall degrading reagent;

(i) then germinating and growing each spore on minimal medium supplemented with nutrients required for growth of haploid spore products and maintaining at 30° C. for 2 days;

(j) replica plating the cells in accordance with step (i) onto sets of minimal medium agar plates, supplemented with combinations of nutrients required to distinguish spore product phenotypes, and maintaining at about 30° C. for 1 day and;

(k) screening the colonies produced in accordance with step (i) for the recombinant gene product corresponding to the marker gene.

2. A process according to claim 1 wherein said second mutant yeast strain is defective in the histidine biosynthetic pathway.

3. A process according to claim 1 wherein said second mutant yeast strain is defective at the normal locus for the gene encoding histidinol dehydrogenase.

4. A process according to claim 1 wherein said first mutant yeast strain is defective at the normal locus for the gene encoding histidinol dehydrogenase, and wild type at any non-native locus for the gene encoding histidinol dehydrogenase.

5. A process in accordance with claim 4 wherein said non-native locus is a gene in the methanol utilization pathway.

6. A process in accordance with claim 4 wherein said non-native locus is AOX2.

7. A process according to claim 1 wherein said first mutant is *Pichia pastoris* strain KM7121 and said second mutant is *Pichia pastoris* PPF1.

* * * * *